(12) United States Patent
Merle et al.

(10) Patent No.: US 8,470,401 B2
(45) Date of Patent: Jun. 25, 2013

(54) USE OF GROUP V METAL CONTAINING PRECURSORS FOR A PROCESS OF DEPOSITING A METAL CONTAINING FILM

(75) Inventors: Nicolas Merle, Villeurbanne (FR); Stéphane Danielle, Villeurbanne (FR); Christian Dussarrat, Wilmington, DE (US); Nicolas Blasco, Grenoble (FR)

(73) Assignee: L'Air Liquide, Socété Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 758 days.

(21) Appl. No.: 12/447,237

(22) PCT Filed: Oct. 19, 2007

(86) PCT No.: PCT/EP2007/061216
§ 371 (c)(1),
(2), (4) Date: Nov. 13, 2009

(87) PCT Pub. No.: WO2008/049790
PCT Pub. Date: May 2, 2008

(65) Prior Publication Data
US 2010/0055310 A1    Mar. 4, 2010

(30) Foreign Application Priority Data
Oct. 26, 2006    (EP) .................................... 06301090

(51) Int. Cl.
*C23C 16/06* (2006.01)
*C23C 16/40* (2006.01)

(52) U.S. Cl.
USPC ................. 427/250; 427/255.31; 427/255.32; 427/255.391; 427/255.394

(58) Field of Classification Search
USPC .............. 427/250, 255.31, 255.393, 255.394, 427/255.32
See application file for complete search history.

(56) References Cited

U.S. PATENT DOCUMENTS

| 4,245,131 | A  | 1/1981 | Schrock |
| 6,268,288 | B1 | 7/2001 | Hautala et al. |

(Continued)

FOREIGN PATENT DOCUMENTS

| EP | 1 884 517 | 2/2008 |
| EP | 1 884 518 | 2/2008 |

(Continued)

OTHER PUBLICATIONS

Mayer, James M., et al., "Hydrogen-Transfer Reactions Which Generate New Imine, Imido, and Trimethylenemethane Complexes of Tantalum". J. Am. Chem. Soc, 1983, 105, 2651-2660.*

(Continued)

*Primary Examiner* — Bret Chen
(74) *Attorney, Agent, or Firm* — Patricia E. McQueeney (57) ABSTRACT

The disclosure is directed to a process for depositing a group V metal containing film on a substrate by introducing a substrate into a reactor; preferably heating the substrate at a temperature above 150° C.; feeding a compound of the formula (Ia) or of the formula (Ib), or a mixture of said compounds thereof in the vapor phase into the reactor; optionally feeding a second compound of the formula (Ia) or of the formula (Ib), or a second mixture of said compounds thereof in vapor phase into the reactor; and thereby depositing the group V metal containing film onto said substrate.

22 Claims, 1 Drawing Sheet

U.S. PATENT DOCUMENTS

| | | | |
|---|---|---|---|
| 6,368,398 | B2 | 4/2002 | Vaartstra |
| 6,379,748 | B1 | 4/2002 | Bhandari et al. |
| 6,491,978 | B1 * | 12/2002 | Kalyanam ............ 427/255.394 |
| 6,503,561 | B1 | 1/2003 | Senzaki et al. |
| 6,593,484 | B2 | 7/2003 | Yasuhara et al. |
| 6,616,972 | B1 | 9/2003 | Senzaki et al. |
| 6,743,473 | B1 | 6/2004 | Parkhe et al. |
| 7,193,098 | B1 * | 3/2007 | Lucey et al. ..................... 556/1 |
| 7,348,445 | B2 * | 3/2008 | Peters et al. ................. 556/176 |
| 2004/0009307 | A1 | 1/2004 | Koh et al. |
| 2004/0014320 | A1 | 1/2004 | Chen et al. |
| 2004/0219784 | A1 | 11/2004 | Kang et al. |
| 2007/0042213 | A1 | 2/2007 | Reuter et al. |
| 2007/0218683 | A1 * | 9/2007 | Ishizaka et al. ............. 438/648 |
| 2008/0050916 | A1 * | 2/2008 | Yonker et al. ................ 438/685 |
| 2008/0081127 | A1 | 4/2008 | Thompson et al. |
| 2008/0102205 | A1 | 5/2008 | Barry et al. |
| 2008/0213999 | A1 * | 9/2008 | Wagner ........................ 438/660 |
| 2008/0248648 | A1 * | 10/2008 | Thompson et al. .......... 438/681 |
| 2009/0311879 | A1 | 12/2009 | Blasco et al. |
| 2010/0055310 | A1 | 3/2010 | Merle et al. |
| 2011/0195574 | A1 * | 8/2011 | Blasco et al. ................ 438/680 |
| 2011/0244681 | A1 * | 10/2011 | Blasco et al. ................ 438/680 |

FOREIGN PATENT DOCUMENTS

| | | |
|---|---|---|
| EP | 2065390 A1 * | 6/2009 |
| JP | 2001-329367 | 11/2001 |
| JP | 2005 132756 | 5/2005 |
| JP | 2005 132757 | 5/2005 |
| JP | 2007-246513 | 9/2007 |
| KR | 10 2008 0119084 | 6/2010 |
| WO | WO 02 20870 | 3/2002 |

OTHER PUBLICATIONS

International Search Report for PCT/EP2007/061216.

Mayer, J.M. et al. "Hydrogen-transfer reactions which generate new imine, imido, and trimethylenemethane complexes of tantalum." Journal of the American Chemical Society, 105(9), 2651-60, 1983.

Wood, C.D. et al. "Reaction of carbon monoxide with (.eta.5-pentamethylcyclopentadienyl)tetra methyltantalum. Intramolecular reductive coupling of carbon monoxide via an ".eta.2-acetone" intermediate." Journal of the American Chemical Society, 101(18), 5421-2, 1979.

Ahn, H. et al. "High-resolution solid-state 13C NMR studies of chemisorbed organometallics. Chemisportive formation of cation-like and alkylidene organotantalum complexes on high surface area inorganic oxides." Journal of the American Chemical Society, 124(24), 7103-7110, 2002.

Gibson, V.C. et al. "Alkoxide, phenoxide and hydrido-phenoxide compounds of tantalum bearing the pentamethylcyclopentadienyl ligand." Journal of Organometallic Chemistry, 444(1-2), 91-4, 1993.

Mayer, J.M. et al. "Synthesis and reactivity of new polyhydride compounds of tantalum(V)." Journal of the American Chemical Society, 104(8), 2157-65, 1982.

Bitterwolf, T.E. et al., "Improved synthesis of ($\eta^5$-CpR)M(CO)$_4$ compounds and the Nujol matrix photochemistry of ($\eta^5$-C$_5$H$_5$)M(CO)$_4$ and ($\eta^5$-C$_9$H$_7$)M(CO)$_4$, where M=Nb and Ta," Journal of Organometallic Chemistry 557 (1998), pp. 77-92.

Djakovitch, L. et al., "Bridged half-sandwich niobiocenes by intramolecular CH activation," Journal of Organometallic Chemistry, vol. 545-546, Oct. 30, 1997, pp. 399-405.

Djakovitch, L. et al., "Half-sandwich ansa-niobiocenes: synthesis and reactivity," Journal of Organometallic Chemistry, vol. 562, No. 1, Jul. 10, 1998, p. 71-78.

Green, M.L. et al., "Chemical vapor deposition of metals for integrated circuit applications," Journal of Metals 37 (1985) 63, pp. 63-71.

Herrmann, W.A. et al., "Structure dynamics in novel ansa-metal-locenes of niobium and tantalum," Agnew. Chem. Int. Ed. Engl. 1996, 35 No. 17, pp. 1951-1953.

Humphries, M.J. et al., "Niobium $\eta$-cyclopentadienyl compounds with imido and amido ligands derived from 2,6-dimethylaniline," J. Chem. Soc., Dalton Trans., 2000, pp. 4044-4051.

Humphries, M.J. et al., "Niobium $\eta$-cyclopentadienyl compounds with imido and amido ligands derived from tert-butylamine," J. Chem. Soc., Dalton Trans, 2000, pp. 4555-4562.

Ritala, M. et al., "Atomic Layer Deposition Handbook," Academic Press, New York (2002), pp. 103-159.

Written Opinion for corresponding PCT/EP2007/061216, Jan. 15, 2008.

EP Search Report for related EP 06 30 5649, Mar. 12, 2009.

International Search Report and Written Opinion for related PCT/EP2009/062964, Nov. 16, 2009.

International Search Report and Written Opinion for related PCT/EP2009/059067, Sep. 11, 2009.

* cited by examiner

USE OF GROUP V METAL CONTAINING PRECURSORS FOR A PROCESS OF DEPOSITING A METAL CONTAINING FILM

CROSS-REFERENCES TO RELATED APPLICATIONS

This application is a 371 of International PCT Application PCT/EP2007/061216, filed Oct. 19, 2007.

STATEMENT REGARDING FEDERALLY SPONSORED RESEARCH OR DEVELOPMENT

Not Applicable
The names of the parties to a joint research agreement
Not Applicable
Reference to a "Sequence Listing," a table, or a computer program listing appendix submitted on a compact disc and an incorporation-by-reference of the material on the compact disc
Not Applicable

BACKGROUND OF THE INVENTION

1. Field of the Invention

The invention relates to a new class or chemical compounds and their use in metal containing film deposition.

2. Description of the Related Art

With the shrink of the critical dimensions of the future generation CMOS devices, the introduction of new materials, in particular Tantalum and Niobium, are required. For instance, it is well acknowledged that dual metal gate will be required along to high dielectric constant (high-k) materials for the CMOS gate stack. The metal gate is in particular required to achieve a 0.2 V threshold voltage, thus allowing drastically reduced devices power consumption. To do so, the metal gate approach requires having two metal compounds of different work function, typically ~5 eV for pMOS gate and ~4 eV for nMOS gate. The requirements for a suitable metal gate material generally include: lowest resistivity as possible (however, it is generally always below p-Si for metal compounds), suitable work function (which is drastically affected by additional elements in the metal based film), thermal stability on the high-k gate oxide, adhesion on the high-k and etch selectivity. Group V metal containing films, and in particular Tantalum based materials such as Tantalum carbide, Tantalum silicide, Tantalum silico-nitride, Tantalum carbo-nitride, show promising properties for metal gate application. TaCN has been suggested as a suitable pMOS metal, TaCN work function was estimated to 4.8-5 eV.

Besides, group V metal containing films are used as electrodes (in the case of pure metal or metal nitride), and also as high-k layers (in the case of oxide) in the Metal-Insulator-Metal structures (DRAM . . . ). For example, TaN may be used for electrodes deposition, and $Ta_2O_5$ and $TaO_xN_y$ for high-k layers.

Besides, group V metal containing films find also application in back-end-of-the-line (BEOL) layers of modern semiconductor devices as metal diffusion barriers. In particular, pure group V metals are targeted, such as Ta on TaN for copper diffusion. Nitrogen incorporation also helps reducing the copper diffusion. Tantalum films are currently deposited using a sputtering deposition method, so as to achieve a low-k/TaN-Ta/Cu patterned structure. With the shrinkage of the chip dimensions, sputtering will quickly become inadequate for conformal depositions.

The main industrial options to enable the deposition of such thin films with reasonable throughput and acceptable purity are vapor phase deposition techniques, such as MOCVD (Metal-organic Chemical Vapor Deposition) or ALD (Atomic Layer Deposition). For instance, ALD (or plasma assisted ALD) is generally considered as a suitable method to form the highly conformal films needed for BEOL applications, when associated with a relevant precursor. Metal-organic and halide compounds are required for those processes.

Many Group V precursors have been considered to enable such deposition. Examples can be given as follows:

Halides such as Tantalum pentachloride, $TaCl_5$, have been widely investigated such as disclosed in U.S. Pat. No. 6,268,288 by Hautala et al. However, some by-products generated during the deposition process, such as HCl or $Cl_2$, can cause surface/interface roughness that can be detrimental to the final properties. Moreover, Cl or F impurities are highly detrimental to the final electrical properties. It is therefore expected to find new compounds having sufficient volatility but without containing Cl, F, or Br atoms.

Alkoxides such as penta-ethoxy-Tantalum (PET) are widely used and described. However, they lead to oxygen containing films and are not suitable for the deposition of metal containing films such as nitrides, carbides, carbo-nitrides, silicides which are used in particular as electrodes and which should not contain oxygen even at trace level.

U.S. Pat. No. 6,379,748 discloses an improvement to PET alkyl bonds have been introduced, e.g. by using $TaMe_3(OEt)_2$ instead of $Ta(OEt)_5$ (PET). Volatility was thereby significantly improved without affecting the melting point. However, $TaMe_3(OEt)_2$ does not allow versatile deposition: in particular, oxygen free metal nitride or carbide cannot be obtain.

U.S. Pat. No. 6,368,398 discloses another improvement with the use for instance of $Ta[OC(O)C(CH_3)_3]_5$, however with the same limitation as disclosed here above.

WO 02/20870 discloses the use of tert-butylimido(tris(diethylamido)Tantalum, TBTDET, for the deposition of $Ta_2O_5$ U.S. Pat. No. 6,593,484, US 2004/0219784 disclose a method of deposition of Tantalum nitride films by sequential injection of TBTDET or TAIMATA and other N source. However, their use to deposit Ta, TaC, TaSi films is not possible as they contain nitrogen which is always present in the deposited films.

U.S. Pat. No. 6,379,748 discloses $Ta(Me_3SiCp)_2H_3$, which is a biscyclopentadienyl Ta hydride which is a solid having a low volatility.

Today, there still exist the need for metal organic precursors having a high volatility in order to be in liquid state at room temperature (or close to room temperature) and having a high versatility, i.e. suitable for various applications in the semi-conductor manufacture such as metal gates, electrodes and/or high-k layer in Metal-Insulator-Metal structures for DRAM and/or copper diffusion barriers, or the like in TFT-LCD applications.

BRIEF SUMMARY OF THE INVENTION

According to a first embodiment, the invention relates to a method of depositing metal containing films using at least one compound as a metal precursor of the formula (Ia):

or of the formula (Ib):

Formulas (Ia) and (Ib) wherein,
M is a group V metal selected from Tantalum (Ta), Niobium (Nb) and Vanadium (V), $R_1, R_2, R_3, R_4, R_5, R_6$ and $R_7$; which may be identical or different, are independently chosen from Hydrogen atom, linear or branched alkyl groups having from one to four carbon atoms, linear or branched alkoxy groups having from one to four carbon atoms, linear or branched alkylamide groups having from one to four carbon atoms, linear or branched alkylsilylamide groups having from one to four carbon atoms; either $R'_1, R'_2, R'_3$ and $R'_4$; which may be identical or different, are independently chosen from Hydrogen atom, linear or branched alkyl groups having from one to four carbon atoms, linear or branched alkoxy groups having from one to four carbon atoms, linear or branched alkylamide groups having from one to four carbon atoms or linear or branched alkylsilylamide groups having from one to four carbon atoms; either $R'_1, R'_2$, which may be identical or different, are independently chosen from Hydrogen atom, linear or branched alkyl groups having from one to four carbon atoms, linear or branched alkoxy groups having from one to four carbon atoms, linear or branched alkylamide groups having from one to four carbon atoms or linear or branched alkylsilylamide groups having from one to four carbon atoms; and $R'_3$ and $R'_4$ together represent an oxo group (=O) or an alkyl imino group having from one to four carbon atoms (=N—R)

According to a first particular embodiment the invention relates to a method of depositing a metal containing film using a compound of the formula (Ia) or of the formula (Ib) as defined above, having a melting point lower than or equal to about 35° C., i.e. shall be in liquid form or close to liquid form at room temperature, which makes their delivery easier.

According to a second particular embodiment the invention relates to a method of depositing a metal containing film using a compound of the formula (Ia) or of the formula (Ib) as defined above, having a vapor pressure higher than 1 Torr at 100° C. In order to do so, the man skilled in the art shall select the appropriate molecules in the group of molecules having a lower molecule weight and/or those having a structure, which induces lowered inter molecular forces.

According to a third particular embodiment, in the formula (Ia) or (Ib), $R_1, R_2, R_3, R_4, R_5, R_6$ and $R_7$; which may be identical or different, are independently chosen from Hydrogen atom, linear or branched alkyl groups having from one to four carbon atoms.

According to a fourth particular embodiment, in the formula (Ia) or (Ib), $R'_1, R'_2, R'_3$, and $R'_4$, which may be identical or different, are independently chosen from Hydrogen atom, linear or branched alkyl groups having from one to four carbon atoms.

According to a fifth particular embodiment, in the formula (Ia) or (Ib), M is Tantalum.

According to a sixth particular embodiment, in the formula (Ia), $R_2, R_3, R_4$, and $R_5$, each represent an Hydrogen atom.

According to a seventh particular embodiment, in the formula (Ib), $R_2, R_3, R_4, R_5, R_6$ and $R_7$, each represent an Hydrogen atom.

According to an eight particular embodiment, in the formula (Ia) or (Ib), $R_1$ is chosen from ethyl, isopropyl or tert-butyl.

According to an ninth particular embodiment, in the formula (Ia) or (Ib), $R'_1, R'_2, R'_3$, and $R'_4$ each represent a methyl group.

According to a tenth particular embodiment, in the formula (Ia) or (Ib), $R'_1$ and $R'_2$, which may be identical or different, are independently chosen from methyl or methoxy, and $R'_3$ and $R'_4$ together represent an oxo group (=O) or a tert-butyl imino group (=N-tBu).

Examples of such particular embodiments are:

According to a eleventh particular, the compounds of the formulas (Ia) or (Ib) as defined herein before are selected from the following compounds:

(Isopropyl-Cyclopentadienyl) tetrakis(methy) Tantalum;

(1,5-diisopropyl-pentadienyl) tetrakis(methyl) Tantalum;

(1,3-di-tert-butyl-cyclopentadienyl) tetrakis(methyl) Tantalum;

(Ethyl-Cyclopentadienyl) tetrakis(methyl) Tantalum, (Isopropyl-Cyclopentadienyl) tetrakis(methyl) Vanadium;

(Isopropyl-Cyclopentadienyl) tetrakis(methyl) Niobium;

(1,3-di-tert-butyl-cyclopentadienyl) tetrakis(methyl) Niobium.

According to another embodiment, the invention related to compounds having the characteristic to contain only one cyclopentadienyl ring and 4 alkylamide ligand, said compounds having the formula:

Where:

M is a group V metal selected from Tantalum (Ta), Niobium (Nb) and Vanadium (V),

Each R is independently selected from the group consisting of linear or branched alkyl groups having from one to four carbon atoms, linear or branched alkoxy groups having from one to four carbon atoms, linear or branched alkylamide groups having from one to four carbon atoms, linear or branched alkylsilylamide groups having from one to four carbon atoms;

Each R' are independently selected from the group consisting of Hydrogen atom, linear or branched alkyl groups having from one to four carbon atoms, linear or branched alkoxy groups having from one to four carbon atoms, linear or branched alkylamide groups having from one to four carbon atoms, linear or branched alkylsilylamide groups having from one to four carbon atoms;

Examples of such particular embodiment are:

According to another embodiment, the invention related to compounds having the characteristic to contain only one cyclopentadienyl ring and 4 alkylamide ligand, said compounds having the formula:

(b)

Where:

M is a group V metal selected from Tantalum (Ta), Niobium (Nb) and Vanadium (V), Each R is independently selected from the group consisting of linear or branched alkyl groups having from one to four carbon atoms, linear or branched alkoxy groups having from one to four carbon atoms, linear or branched alkylamide groups having from one to four carbon atoms, linear or branched alkylsilylamide groups having from one to four carbon atoms.

DETAILED DESCRIPTION OF THE INVENTION

The compounds of the formula (Ia) or (Ib) alone or in admixture, are used to deposit films of various compositions (as disclosed herein after) using any well-known deposition method using vapor phase deposition, such as MOCVD (Metal Organic Chemical Vapor Deposition), ALD (atomic layer deposition) and any other deposition method such as PECVD (plasma enhanced chemical vapor deposition) or as pulsed CVD. These new groop V metal precursors are thus useful for pure metal, metallic oxide, oxynitride, nitride and/or silicide film deposition to make electrodes and/or high k layers, and/or copper diffusion barrier layers and the like. In the ALD process the preferred temperature is in the range of 150 to 400° C., more preferably 200 to 350° C., the preferred pulse duration in ALD is 1s and the preferred pressure is in the range of 0.1 Torr to 500 Torr, more preferably from 1 Torr to 100 Torr. In the CVD process, the preferred temperature is in the range of 300° C. to 700° C., more preferably from 300° C. to 500° C., the preferred pressure is in the range of 0.1 Torr to 500 Torr, preferably from 1 Torr to 100 Torr and the preferred carrier gas is selected from N$^2$, He, Ar, H2, more preferably Ar or N2. The preferred N2 canister flow is in the 30-200 sccm range, preferably 50 to 100 sccm.

In the PECVD process, the preferred temperature is in the range of 300° C. to 700° C., more preferably from 300° C. to 500° C., the preferred pressure is in the range of 0.1 Torr to 500 Torr, preferably from 1 Torr to 100 Torr, the preferred carrier gas is selected from N2, He, Ar, H2, more preferably Ar or N2 and the preferred N2 canister flow is in the 30-200 sccm range, preferably 50 to 100 sccm. H or NH radicals are produced by a remote plasma system and used as co-reactant.

In these above mentioned uses, any of the compound of the formula (Ia) or of the formula (Ib) as defined above, can be used alone or in admixture with one or several other compounds of the said formulas (Ia) or (Ib) and/or with any appropriate additive which are useful when depositing a metal containing film as provided hereafter. According to a first particular embodiment the invention relates to a use as defined above of such an admixture having a melting point lower than or equal to about 35° C., i.e. shall be in liquid form or close to liquid form at room temperature, which makes their delivery easier, and or having a vapor pressure higher than 1 Torr at 100° C.

Various films can be obtained on a substrate by using the precursors described here above, such as nitrides, carbides, silicides, nitro-silicides (MSiN), oxydes (e.g. MeO$_j$), oxynitrides (MO$_x$N$_y$) and oxynitrides from two different metals M$_1$ and M$_2$ (M$^1$M$^2$O$_x$N$_y$).

The invention also relates to a process for depositing a group V metal containing film on a substrate comprising the steps of:
 introducing a substrate into a reactor,
 preferably heating the substrate at a temperature above 150° C.;
 feeding a compound of the formula (Ia) or of the formula (Ib) as disclosed herein before or of a mixture of said compounds thereof in the vapor phase into the reactor;
 optionally feeding at least one second precursor in vapor phase into the reactor;
 depositing a film containing at least one of said group V metal.

If pure metal needs to be deposited onto the surface of the substrate, then no second precursor injection is needed.

However, if a film of nitride, carbide, silicide, nitro-silicide, oxyde, oxynitrides or the like is needed, then such second precursor injection may be necessary, providing the adequate species to obtain the final desired composition of the film.

TaN: preferred reactants are NH3, N2H4, methylhydrazine
TaSi: preferred second precursor is SiH4,
TaSiN: preferred second precursor is TSA and NH3, TriDMAS and NH3
TaO: preferred oxygen source if O3
TaHfO: preferred second precursor is TEMAH
TaC: precursor can be used alone, C2H4 can also be used to enhance C content.

The process according to the invention may be summarized according to

Figure 2:
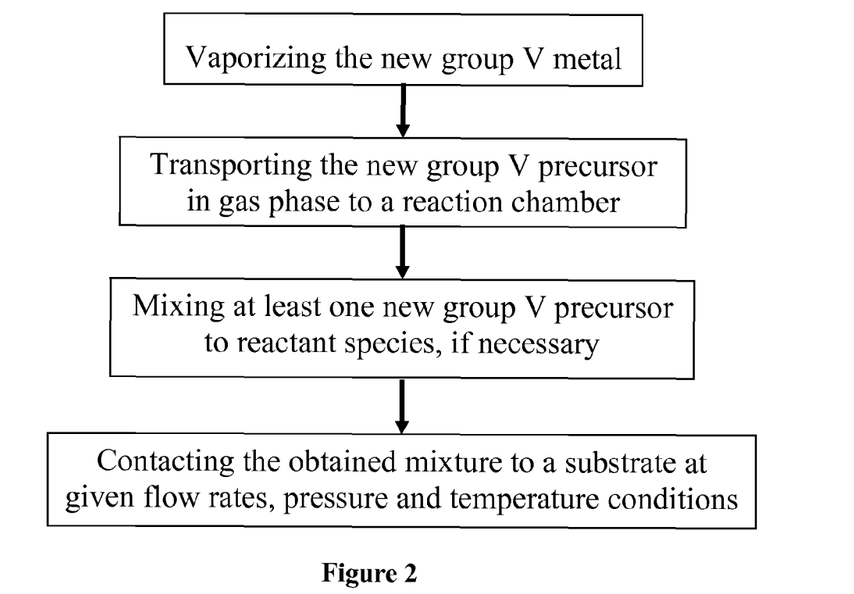
FIG. 2 shows a flow diagram of the steps of a preferred process of the invention.

FIG. 2. In accordance with one embodiment, the vaporization of the new metal source is realized by introducing a carrier gas into a heated container containing the said new metal source. The container is preferably heated at a temperature allowing to get the said metal source in liquid phase and at a sufficient vapor pressure. The carrier gas can be selected, without limitation, from Ar, He, $H_2$, $N_2$ or mixtures of them. The said metal source can be mixed to a solvent or to another metal source or to a mixture of them in the container. The container can for instance be heated at temperatures in the range of 80-110° C. Those skilled in the art will consider that the temperature of the container can be adjusted to control the amount of precursor vaporized.

In accordance with another embodiment, the said metal source is fed in liquid state to a vaporizer where it is vaporized. The said metal source can be mixed to a solvent. The said metal source can be mixed to another metal source. The said mixture of metal sources can be mixed to a solvent or a mixture of solvent. The said metal source can be mixed to a stabilizer.

The vaporized metal source is there after introduced into a reaction chamber where it is contacted to a substrate. The substrate can be heated to a sufficient temperature to obtain the desired film at sufficient growth rate and with desired physical state and composition. Typical temperature range from 150° C. to 600° C. Preferably the temperature is lower or equal to 450° C. The pressure in the reaction chamber is controlled to obtain the desired metal containing film at sufficient growth rate. Typical pressure range from 1 m Ton to 100 Torr or higher.

According to another embodiment, it is possible to mix the metal source to a reactant species prior to the introduction of the mixture into the reaction chamber.

In another embodiment of the invention, the metal source may be mixed to a reactant species in the reaction chamber.

According to a further embodiment, the metal source and the reactant species are introduced simultaneously (chemical vapor deposition), sequentially (atomic layer deposition) or any combination thereof (one example is to introduce the metal source and the other metal source together in one pulse and oxygen in a separate pulse [modified atomic layer deposition]; another example is to introduce oxygen continuously and to introduce the metal sources by pulse (pulsed-chemical vapor deposition).

It is also possible to introduce the reactant species into a plasma system localized remotely from the reaction chamber to decompose these species into radicals before their introduction into the reaction chamber.

According to a further embodiment, wherein the targeted metal based film contains oxygen, such as for example, without limitation metal, oxide or metal oxy-nitride, the reactant species shall include an oxygen source which is selected from the group comprising oxygen ($O_2$), oxygen radicals (for instance O. or OH.), for instance generated by a remote plasma, ozone ($O_3$), NO, $N_2O$, $NO_2$, moisture ($H_2O$) and $H_2O_2$ or any mixture thereof;

According to still a further embodiment, wherein the targeted metal based film contains nitrogen, such as for example metal nitride or metal carbo-nitride, the reactant species include a nitrogen source which is selected from, but not limited to, nitrogen ($N_2$), ammonia, hydrazine and alkyl derivatives, N-containing radicals (for instance N, NH, $NH_2$.), NO, $N_2O$, $NO_2$, amines.

If the targeted metal based film contains carbon, such as for example without limitation metal carbide or metal carbonitride, the reactant species include a carbon source which is selected from, but not limited to, methane, ethane, propane, butane, ethylene, propylene, t-butylene, isobutylene, $CCl_4$.

If the targeted metal based film contains silicon, such as for example metal silicide, silico-nitride, silicate, silico-carbonitride, the reactant species shall include a silicon source which is selected from the group comprising $SiH_4$, $Si_2H_6$, $Si_3H_8$, TriDMAS, BDMAS, BDEAS, TDEAS, TDMAS, TEMAS, $(SiH_3)_3N$, $(SiH_3)_2O$, trisilylamine, disiloxane, trisilylamine, disilane, trisilane, a alkoxysilane $SiH_x(OR^1)_{4-x}$, a silanol $Si(OH)_x(OR^1)_{4-x}$ (preferably $Si(OH)(OR^1)_3$; more preferably $Si(OH)(OtBu)_3$ an aminosilane $SiH_x(NR^1R^2)_{4-x}$ (where x is comprised between 0 and 4; $R^1$ and $R^2$ are independently H or a C1-C6 carbon chain, either linear, branched or cyclic; preferably TriDMAS $SiH(NMe_2)_3$, BTBAS $SiH_2(NHtBu)_2$); BDEAS $SiH_2(NEt_2)_2$) and mixtures thereof. The targeted film can alternatively contain Germanium. The above-mentioned Si containing sources, may be replaced by similar Ge containing sources.

It is quite possible to mix a metal source to another metal source to deposit a multi-metal containing film, prior to their introduction into the reaction chamber or to simultaneously introduce into the reaction chamber, these metal sources and mix them together and/or with other reactant species in the reaction chamber.

But it is also possible to introduce the first metal source, the second metal source and the reactant species in the reaction chamber simultaneously (chemical vapor deposition), sequentially (atomic layer deposition) or any combination thereof (one example is to introduce the first metal source and the second metal sources together in one pulse and oxygen in a separate pulse [modified atomic layer deposition]; another example is to introduce oxygen continuously and to introduce the metal source by pulse (pulsed-chemical vapor deposition).

The second metal source shall be selected from the group comprising lanthanide and rare-earth metal source (Sc, Y, La, Ce, Pr, Nd, Gd . . . ) source such as rare earth diketonates Ln(-O—C($R^1$)—C($R^2$)—C($R^3$)—O—)(—O—C($R^4$)—C ($R^5$)—C($R^6$)—O—)(—O—C($R^7$)—C($R^8$)—C($R^9$)—O—), where each R' is independently H or a C1-C6 carbon chain, either linear, branched or cyclic), a cyclopentadienyl Ln(R'Cp)($R^2$Cp)($R^3$Cp) (where each R' is independently H or a C1-C6 carbon chain, either linear, branched or cyclic), Ln(N$R^1R^2$)(N$R^3R^4$)(N$R^5R^6$) and mixtures thereof. The second metal source can alternatively be an aluminum source, selected from the group consisting of trimethyl aluminum, dimethyl aluminum hydride, an alkoxyalane Al$R^i_x$(OR.)$_{3-x}$ (where x is comprised between 0 and 3; $R^1$ and $R^2$ are independently H or a C1-C6 carbon chain, either linear, branched or cyclic; preferably Al$R^1R^2$(OR.), most preferably AlMe$_2$(OiPr)), an amidoalane Al$R^i_x$(NR'R'')$_3$, (where x is comprised between 0 and 3; $R^1$ and $R^2$ are independently H or a C1-C6 carbon chain, either linear, branched or cyclic) and mixtures thereof. The other metal source can alternatively be a tungsten, molybdenum source. The other metal source can alternatively be a hafnium, zirconium or titanium source such as M(O$R^1$)$_4$ or other alkoxide-containing metal sources, M(N$R^1R^2$)$_4$, or adducts containing these species. The second metal source can alternatively be a divalent metal source (preferably Mg, Ca, Zn) selected from, but not limited to metal β-diketonates or adducts containing these species.

The reactants can be introduced simultaneously (chemical vapor deposition), sequentially (atomic layer deposition) any combination thereof.

Example 1

Group V Metal Compounds

Hereafter are listed some of the precursors of the formula (Ia) or (Ib) as defined herein before (cp means cyclopentadienyl, C$_5$ means pentadienyl): Ta(MeCp)Me$_4$, Ta(EtCp)Me$_4$, Ta(iPrCp)Me$_4$, Ta(tBuCp)Me$_4$, Ta(Me$_2$ Cp)Me$_4$, Ta(Et$_2$ Cp)Me$_4$, Ta(iPr$_2$ Cp)Me$_4$, Ta(tBu$_2$ Cp)Me$_4$, Ta(Et$_5$C$_5$)Me$_4$, Ta(iPr$_5$C$_5$)Me$_4$, Ta(MeCp)Et$_4$, Ta(EtCp)Et$_4$, Ta(iPrCp)Et$_4$, Ta(tBuCp)Et$_4$, Ta(Me$_2$ Cp)Et$_4$, Ta(Et$_2$ Cp)Et$_4$, Ta(iPr$_2$ Cp)Et$_4$, Ta(tBu$_2$ Cp)Et$_4$, Ta(Et$_5$C$_5$)Et$_4$, Ta(iPr$_5$C$_5$)Et$_4$, Ta(MeCp)Me$_2$Et$_2$, Ta(EtCp)Me$_2$Et$_2$, Ta(iPrCp)Me$_2$Et$_2$, Ta(tBuCp)Me$_2$Et$_2$, Ta(Me$_2$ Cp)Me$_2$Et$_2$, Ta(Et$_2$ Cp)Me$_2$Et$_2$, Ta(iPr$_2$ Cp)Me$_2$Et$_2$, Ta(tBu$_2$ Cp)Me$_2$Et$_2$, Ta(Et$_5$C$_5$)Me$_2$Et$_2$, Ta(iPr$_5$C$_5$)Me$_2$Et$_2$, Ta(MeEtCp)Me$_4$, Ta(MeCp)(NEtMe)$_4$, Ta(EtCp)(NEtMe)$_4$, Ta(iPrCp)(NEtMe)$_4$, Ta(tBuCp)(NEtMe)$_4$, Ta(Me$_2$ Cp)(NEtMe)$_4$, Ta(Et$_2$ Cp)(NetMe)$_4$, Ta(iPr$_2$ Cp)(NEtMe)$_4$, Ta(tBu$_2$ Cp)(NEtMe)$_4$, Ta(Et$_5$C$_5$)(NEtMe)$_4$, Ta(iPr$_5$C$_5$)(NEtMe)$_4$, Ta(MeCp)(NMe$_2$)$_4$, Ta(EtCp)(NMe$_2$)$_4$, Ta(iPrCp)(NMe$_2$)$_4$, Ta(tBuCp)(NMe$_2$)$_4$, Ta(Me$_2$ Cp)(NMe$_2$)$_4$, Ta(Et$_2$ Cp)(NMe$_2$)$_4$, Ta(iPr$_2$ Cp)(NMe$_2$)$_4$, Ta(tBu$_2$ Cp)(NMe$_2$)$_4$, Ta(Et$_5$C$_5$)(NMe$_2$)$_4$, Ta(iPr$_5$C$_5$)(NMe$_2$)$_4$, Ta(MeCp)(NEt$_2$)$_4$, Ta(EtCp)(NEt$_2$)$_4$, Ta(iPrCp)(NEt$_2$)$_4$, Ta(tBuCp)(NEt$_2$)$_4$, Ta(Me$_2$ Cp)(NEt$_2$)$_4$, Ta(Et$_2$ Cp)(NEt$_2$)$_4$, Ta(iPr$_2$ Cp)(NEt$_2$)$_4$, Ta(tBu$_2$ Cp)(NEt$_2$)$_4$, Ta(Et$_5$C$_5$)(NEt$_2$)$_4$, Ta(iPr$_5$C$_5$)(NEt$_2$)$_4$, Ta(MeCp)(OMe)$_4$, Ta(EtCp)(OMe)$_4$, Ta(iPrCp)(OMe)$_4$, Ta(tBuCp)(OMe)$_4$, Ta(Me$_2$ Cp)(OMe)$_4$, Ta(Et$_2$ Cp)(OMe)$_4$, Ta(iPr$_2$ Cp)(OMe)$_4$, Ta(tBu$_2$ Cp)(OMe)$_4$, Ta(Et$_5$C$_5$)(OMe)$_4$, Ta(iPr$_5$C$_5$)(OMe)$_4$, Nb(MeCp)Me$_4$, Nb(EtCp)Me$_4$, Nb(iPrCp)Me$_4$, Nb(tBuCp)Me$_4$, Nb(Me$_2$ Cp)Me$_4$, Nb(Et$_2$ Cp)Me$_4$, Nb(iPr$_2$ Cp)Me$_4$, Nb(tBu$_2$ Cp)Me$_4$, Nb(Et$_5$C$_5$)Me$_4$, Nb(iPr$_5$C$_5$)Me$_4$, Nb(MeCp)Et$_4$, Nb(EtCp)Et$_4$, Nb(iPrCp)Et$_4$, Nb(tBuCp)Et$_4$, Nb(Me$_2$ Cp)Et$_4$, Nb(Et$_2$ Cp)Et$_4$, Nb(iPr$_2$ Cp)Et$_4$, Nb(tBu$_2$ Cp)Et$_4$, Nb(Et$_5$C$_5$)Et$_4$, Nb(iPr$_5$C$_5$)Et$_4$, Nb(MeCp)Me$_2$Et$_2$, Nb(EtCp)Me$_2$Et$_2$, Nb(iPrCp)Me$_2$Et$_2$, Nb(tBuCp)Me$_2$Et$_2$, Nb(Me$_2$ Cp)Me$_2$Et$_2$, Nb(Et$_2$ Cp)Me$_2$Et$_2$, Nb(iPr$_2$ Cp)Me$_2$Et$_2$, Nb(tBu$_2$ Cp)Me$_2$Et$_2$, Nb(Et$_5$C$_5$)Me$_2$Et$_2$, Nb(iPr$_5$C$_5$)Me$_2$Et$_2$, Nb(MeEtCp)Me$_4$, Nb(MeCp)(NEtMe)$_4$, Nb(EtCp) (NEtMe)$_4$, Nb(iPrCp)(NEtMe)$_4$, Nb(tBuCp)(NEtMe)$_4$, Nb(Me$_2$ Cp)(NEtMe)$_4$, Nb(Et$_2$ Cp)(NEtMe)$_4$, Nb(iPr$_2$ Cp)(NEtMe)$_4$, Nb(tBu$_2$ Cp)(NEtMe)$_4$, Nb(Et$_5$C$_5$)(NEtMe)$_4$, Nb(iPr$_5$C$_5$)(NEtMe)$_4$, Nb(MeCp)(NMe$_2$)$_4$, Nb(EtCp) (NMe$_2$)$_4$, Nb(iPrCp)(NMe$_2$)$_4$, Nb(tBuCp)(NMe$_2$)$_4$, Nb(Me$_2$ Cp)(NMe$_2$)$_4$, Nb(Et$_2$ Cp)(NMe$_2$)$_4$, Nb(iPr$_2$ Cp)(NMe$_2$)$_4$, Nb(tBu$_2$ Cp)(NMe$_2$)$_4$, Nb(Et$_5$C$_5$)(NMe$_2$)$_4$, Nb(iPr$_5$C$_5$) (NMe$_2$)$_4$, Nb(MeCp)(NEt$_2$)$_4$, Nb(EtCp)(NEt$_2$)$_4$, Nb(iPrCp) (NEt$_2$)$_4$, Nb(tBuCp)(NEt$_2$)$_4$, Nb(Me$_2$ Cp)(NEt$_2$)$_4$, Nb(Et$_2$ Cp)(NEt$_2$)$_4$, Nb(iPr$_2$ Cp)(NEt$_2$)$_4$, Nb(tBu$_2$ Cp)(NEt$_2$)$_4$, Nb(Et$_5$C$_5$)(NEt$_2$)$_4$, Nb(iPr$_5$C$_5$)(NEt$_2$)$_4$, Nb(MeCp)(OMe)$_4$, Nb(EtCp)(OMe)$_4$, Nb(iPrCp)(OMe)$_4$, Nb(tBuCp)(OMe)$_4$, Nb(Me$_2$ Cp)(OMe)$_4$, Nb(Et$_2$ Cp)(OMe)$_4$, Nb(iPr$_2$ Cp) (OMe)$_4$, Nb(tBu$_2$ Cp)(OMe)$_4$, Nb(Et$_5$C$_5$)(OMe)$_4$, Nb(iPr$_5$C$_5$)(OMe)$_4$, V(MeCp)Me$_4$, V(EtCp)Me$_4$, V(iPrCp) Me$_4$, V(tBuCp)Me$_4$, V(Me$_2$ Cp)Me$_4$, V(Et$_2$ Cp)Me$_4$, V(iPr$_2$ Cp)Me$_4$, V(tBu$_2$ Cp)Me$_4$, V(Et$_5$C$_5$)Me$_4$, V(iPr$_5$C$_5$)Me$_4$, V(MeCp)Et$_4$, V(EtCp)Et$_4$, V(iPrCp)Et$_4$, V(tBuCp)Et$_4$, V(Me$_2$ Cp)Et$_4$, V(Et$_2$ Cp)Et$_4$, V(iPr$_2$ Cp)Et$_4$, V(tBu$_2$ Cp)Et$_4$, V(Et$_5$C$_5$)$_4$, V(iPr$_5$C$_5$)Et$_4$, V(MeCp)Me$_2$Et$_2$, V(EtCp) Me$_2$Et$_2$, V(iPrCp)Me$_2$Et$_2$, V(tBuCp)Me$_2$Et$_2$, V(Me$_2$ Cp)Me$_2$Et$_2$, V(Et$_2$ Cp)Me$_2$Et$_2$, V(iPr$_2$ Cp)Me$_2$Et$_2$, V(tBu$_2$ Cp)Me$_2$Et$_2$, V(Et$_5$C$_5$)Me$_2$Et$_2$, V(iPr$_5$C$_5$)Me$_2$Et$_2$, V(MeEtCp)Me$_4$, V(MeCp)(NEtMe)$_4$, V(EtCp)(NEtMe)$_4$, V(iPrCp)(NEtMe)$_4$, V(tBuCp)(NEtMe)$_4$, V(Me$_2$ Cp) (NEtMe)$_4$, V(Et$_2$ Cp)(NetMe)$_4$, V(iPr$_2$ Cp)(NEtMe)$_4$, V(tBU$_2$ Cp)(NEtMe)$_4$, V(Et$_5$C$_5$)(NEtMe)$_4$, V(iPr$_5$C$_5$) (NEtMe)$_4$, V(MeCp)(NMe$_2$)$_4$, V(EtCp)(NMe$_2$)$_4$, V(iPrCp) (NMe$_2$)$_4$, V(tBuCp)(NMe$_2$)$_4$, V(Me$_2$ Cp)(NMe$_2$)$_4$, V(Et$_2$ Cp) (NMe$_2$)$_4$, V(iPr$_2$ Cp)(NMe$_2$)$_4$, V(tBu$_2$ Cp)(NMe$_2$)$_4$, V(Et$_5$C$_5$) (NMe$_2$)$_4$, V(iPr$_5$C$_5$)(NMe$_2$)$_4$, V(MeCp)(NEt$_2$)$_4$, V(EtCp) (NEt$_2$)$_4$, V(iPrCp)(NEt$_2$)$_4$, V(tBuCp)(NEt$_2$)$_4$, V(Me$_2$ Cp) (NEt$_2$)$_4$, V(Et$_2$ Cp)(NEt$_2$)$_4$, V(iPr$_2$ Cp)(NEt$_2$)$_4$, V(tBu$_2$ Cp) (NEt$_2$)$_4$, V(Et$_5$C$_5$)(NEt$_2$)$_4$, V(iPr$_5$C$_5$)(NEt$_2$)$_4$, V(MeCp) (OMe)$_4$, V(EtCp)(OMe)$_4$, V(iPrCp)(OMe)$_4$, V(tBuCp) (OMe)$_4$, V(Me$_2$ Cp)(OMe)$_4$, V(Et$_2$ Cp)(OMe)$_4$, V(iPr$_2$ Cp) (OMe)$_4$, V(tBu$_2$ Cp)(OMe)$_4$, V(Et$_5$C$_5$)(OMe)$_4$, V(iPr$_5$C$_5$) (OMe)$_4$, V(iPrCp)(=O)(OMe)$_2$, V(iPrCp)(=O)(OEt)$_2$, Ta(iPrCp)(=NtBu)Me$_2$, Ta(iPrCp)2(=NiPr)Me$_2$ Example 2

MOCVD of TaC using Ta(iPrCp)Me$_4$

Ta(iPrCp)Me$_4$ is stored into a container. The container is heated at 90° C. and N$_2$ is used as carrier gas at a flow of 100 sccm. The pressure in the container is controlled at 50 Torr. Ta(iPrCp)Me$_4$ is mixed to a H$_2$/N$_2$ gas mixture into the reaction chamber. The substrate is heated at 450° C. The pressure inside the reactor is set at 20 Torr. A film of Tantalum carbide is obtained.

To increase the carbon content, C$_2$H$_4$ can be simultaneously introduced in the reaction chamber.

Similar experiments can be performed with Nb and V analogs.

Example 3

MOCVD of TaSi using Ta(iPrCp)Me$_4$

Ta(iPrCp)Me$_4$ is stored into a container. The container is heated at 90° C. and N$_2$ is used as carrier gas at a flow of 100 sccm. The pressure in the container is controlled at 50 Torr. Ta(iPrCp)Me$_4$ is mixed to a SiH$_4$/N$_2$ gas mixture into the reaction chamber. The substrate is heated at 500° C. The pressure inside the reaction chamber is set at 10 Torr. A film of Tantalum silicide is obtained.

Similar experiments can be performed with Nb and V analogs.

Example 4 CL MOCVD of $Ta_2O_5$ using $Ta(iPrCp)Me_4$ $Ta(iPrCp)Me_4$ is stored into a container. The container is heated at 90° C. and $N_2$ is used as carrier gas at a flow of 100 sccm. The pressure in the container is controlled at 50 Torr. $Ta(iPrCp)Me_4$ is mixed to an $O_2/N_2$ gas mixture into the reaction chamber. The substrate is heated at 450° C. The pressure inside the reaction chamber is set at 20 Torr. A film of Tantalum oxide is obtained.

Similar experiments can be performed with Nb and V analogs.

Example 5

MOCVD of HfTaOx using $Ta(iPrCp)Me_4$ and another Hf Precursor $Ta(iPrCp)Me_4$ is stored into a container. The container is heated at 90° C. and $N_2$ is used as carrier gas at a flow of 100 sccm. Tetrakis(ethylmethylamino)Hafnum, TEMAH, is stored in another container, heated at 90° C. and a $N_2$ carrier is passed through this second container at 100 sccm. The pressure in both containers is controlled at 50 Torr. Both precursors are simultaneously fed into the reaction chamber. A $O_2/N_2$ gas mixture is simultaneously introduced into the reaction chamber. The substrate is heated at 450° C. The pressure inside the reaction chamber is set at 20 Torr. A film of Tantalum hafnium oxide is obtained.

Similar experiments can be performed with Nb and V analogs.

Example 6

ALD of HfTaOx using $Ta(iPrCp)Me_4$ and another Hf Precursor $Ta(iPrCp)Me_4$ is stored into a container. The container is heated at 90° C. and N2 is used as carrier gas at a flow of 100 sccm. Tetrakis(ethylmethylamino)Hafnum, TEMAH, is stored in another container, heated at 90° C. and a $N_2$ carrier is passed through this second container at 100 sccm. The pressure in both containers is controlled at 50 Torr. $O_3$ is used as oxygen source. The substrate is heated at 300° C. The precursors are sequentially introduced into the reaction chamber: during the first step a pulse of $Ta(iPrCp)Me_4$ is introduced during 2s, followed by a 2s $N_2$ purge. A pulse of $O_3$ is then introduced into the reaction chamber during 2s, followed by a 2s $N_2$ purge. A pulse of TEMAH is then introduced into the reaction chamber during 2s, followed by a 2s $N_2$ purge. A pulse of $O_3$ is then introduced into the reaction chamber during 2s. The first step is then done again. 100 cycles are performed this way. A film of Tantalum hafnium oxide is obtained.

Similar experiments can be performed with Nb and V analogs.

Example 7

Synthesis of $Ta(iPrCp)Me_4$ $Ta(iPrCp)Me_4$ is prepared in 3 steps. $TaCl_2Me_3$ is prepared by the reaction of LiMe over $TaCl_5$. $Ta(iPrCp)ClMe_3$ is then prepared by the reaction of Li(iPrCp) on $TaCl_2Me_3$. $Ta(iPrCp)Me_4$ is finally obtained by the reaction of LiMe over $Ta(iPrCp)ClMe_3$. The resulting compound is purified by distillation enough times to obtain in reasonable yield a compound of sufficient purity to be used in the semiconductor industry.

Example 8

Synthesis of $Ta(tBu_2Cp)Me_4$

A solution of t-Bu2C5H3SiMe3 (4.42 g, 17.6 mmol) in toluene is slowly added at −78° C. to a suspension of TaCl5 (6.31 g, 17.6 mmol) in toluene. The reaction mixture is then allowed to react at room temperature for further 12 h. The yellow precipitate of (t-Bu2 Cp)TaCl4 is collected washed with pentane and dried under vacuum. Yield 7.61 g, 86%.

Ta(t-Bu2 Cp)Me4 is then obtained by the reaction of LiMe over (t-Bu2 Cp)TaCl4.

Example 9

Synthesis of $Ta(tBu_2 Cp)(NMe_2)_4$

A solution of t-Bu2C5H3SiMe3 (4.42 g, 17.6 mmol) in toluene is slowly added at −78° C. to a suspension of TaCl5 (6.31 g, 17.6 mmol) in toluene. The reaction mixture is then allowed to react at room temperature for further 12 h. The yellow precipitate of (t-Bu2 Cp)TaCl4 is collected washed with pentane and dried under vacuum. Yield 7.61 g, 86%.

Ta(t-Bu2 Cp)Me4 is then obtained by the reaction of LiNMe2 (commercially available) over (t-Bu2 Cp)TaCl4.

Example 10

Thermal Gravimetric Analysis of $Ta(tBu_2 Cp)Me_4$

Figure 1:
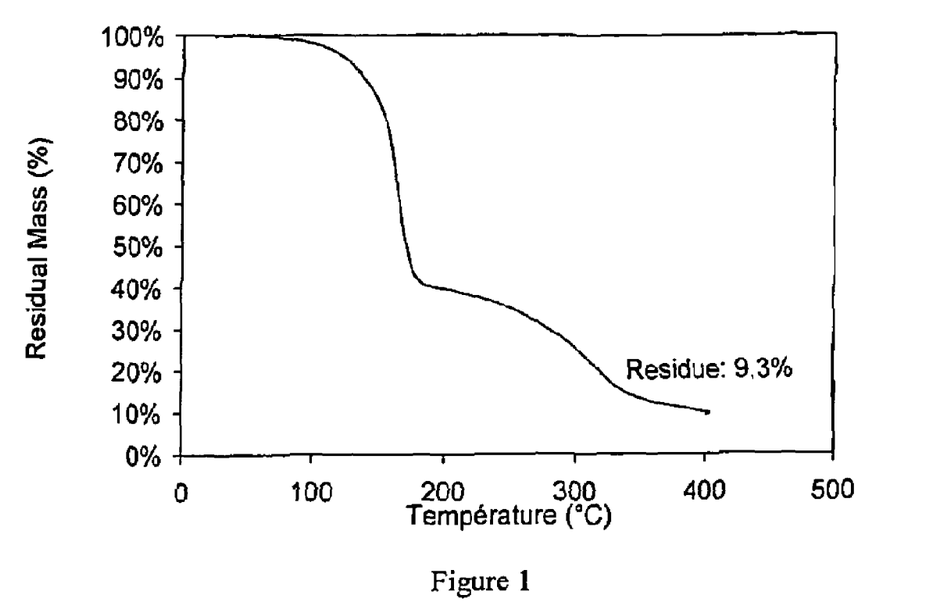
FIG. 1 shows the results of a thermal gravimetric analysis for Ta(tBu$_2$ Cp)Me$_4$.

A sample of 35.445 mg of $Ta(tBu_2 Cp)Me_4$ was placed in a crucible in a thermal gravimetric apparatus. Temperature was raised at 10° C./min under reduced pressure condition. Mass loss and sample heat flow were measured by thermal gravimetric analysis and differential scanning calorimetry. TGA curve is shown in FIG. 1.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for depositing a group V metal containing film on a substrate comprising the steps of:
   introducing a substrate into a reactor;
   feeding a compound of the formula (Ia) or of the formula (Ib), or a mixture of said compounds thereof in the vapor phase into the reactor;

(Ia)

(Ib)

wherein:
M is a group V metal selected from Tantalum (Ta), Niobium (Nb) and Vanadium (V);
$R_1, R_2, R_3, R_4, R_5, R_6$ and $R_7$; which may be identical or different, are independently chosen from Hydrogen atom, linear or branched alkyl groups having from one to four carbon atoms, linear or branched alkoxy groups having from one to four carbon atoms, linear or branched alkylamide groups having from one to four carbon atoms, linear or branched alkylsilylamide groups having from one to four carbon atoms;
either $R'_1, R'_2, R'_3$ and $R'_4$; which may be identical or different, are independently chosen from Hydrogen atom, linear or branched alkyl groups having from one to four carbon atoms, linear or branched alkoxy groups having from one to four carbon atoms, linear or branched alkylamide groups having from one to four carbon atoms or linear or branched alkylsilylamide groups having from one to four carbon atoms;
or and $R'_4$ together represent an oxo group (=O) or alkyl imino group having from one to four carbon atoms (=N—R);
depositing the group V metal containing film onto said substrate.

2. The process of claim 1, further comprising the step of injecting into the reactor a reactant selected from the group consisting of $NH_3$, $N_2H_4$, methylhydrazine and any mixture thereof, wherein the group V metal containing film is TaN.

3. The process of claim 1, further comprising the step of feeding into the reactor a Si containing precursor, wherein the group V metal containing film is TaSi.

4. The process of claim 3, wherein the Si containing precursors is $SiH_4$.

5. The process of claim 1, further comprising the step of feeding into the reactor a Si containing precursor and a reactant, wherein the group V metal containing film is TaSiN.

6. The process of claim 5, wherein the Si containing precursor is trisilylamine or TriDMAS and the reactant is $NH_3$.

7. The process of claim 1, further comprising the step of injecting into the reactor an oxygen comprising reactant, wherein the group V metal containing film is TaO.

8. The process of claim 7, wherein the oxygen comprising reactant is $O_3$.

9. The process of claim 1, further comprising the step of injecting into the reactor an oxygen comprising reactant and a Hafnium containing precursor, wherein the group V metal containing film is TaHfO.

10. The process of claim 9, wherein the hafnium containing precursor is TEMAHf.

11. The process of claim 1, wherein the group V metal containing film is TaC, further comprising the step of injecting the compound alone or additionally injecting a carbon precursor when more than about 30% vol. of carbon is needed in the group V metal containing film.

12. The process of claim 11, wherein the carbon precursor is $C_2H_4$.

13. The process of claim 1, wherein $R_1, R_2, R_3, R_4, R_5, R_6$ and $R_7$, which may be identical or different, are independently chosen from Hydrogen atom or linear or branched alkyl groups having from one to four carbon atoms.

14. The process of claim 1, wherein $R'_1, R'_2, R'_3,$ and $R'_4$, which may be identical or different, are independently chosen from Hydrogen atom or linear or branched alkyl groups having from one to four carbon atoms.

15. The process of claim 1, wherein $R_2, R_3, R_4,$ and $R_5$, each represent a Hydrogen atom.

16. The process of claim 1, wherein $R_2, R_3, R_4, R_5, R_6$ and $R_7$, each represent a Hydrogen atom.

17. The process of claim 1, wherein $R_1$ is chosen from ethyl, isopropyl or tert-butyl.

18. The process of claim 1, wherein $R'_1, R'_2, R'_3,$ and $R'_4$ each represent a methyl group.

19. The process of claim 1, wherein $R'_1$ and $R'_2$, which may be identical or different, are independently chosen from methyl or methoxy, and $R'_3$ and $R'_4$ together represent an oxo group (=O) or a tert-butyl imino group (=N-tBu).

20. The process of claim 1, wherein the compound comprises at least one member selected from the group consisting of:
(Isopropyl-Cyclopentadienyl) tetrakis(methyl) Tantalum;
(1,5-diisopropyl-pentadienyl) tetrakis(methyl) Tantalum;
(1,3-di-tert-butyl-cyclopentadienyl) tetrakis(methyl) Tantalum;
(Ethyl-cyclopentadienyl) tetrakis(methyl) Tantalum;
(Isopropyl-Cyclopentadienyl) tetrakis(methyl) Vanadium;
(Isopropyl-Cyclopentadienyl) tetrakis(methyl) Niobium; and
(1,3-di-tert-butyl-cyclopentadienyl) tetrakis(methyl) Niobium.

21. The process of claim 1, further comprising a step of heating the substrate at a temperature above 150° C.

22. The process of claim 1, further comprising a step of feeding a second compound of the formula (Ia) or of the formula (Ib), or a second mixture of said compounds thereof in vapor phase into the reactor.

* * * * *

UNITED STATES PATENT AND TRADEMARK OFFICE
CERTIFICATE OF CORRECTION

PATENT NO. : 8,470,401 B2  
APPLICATION NO. : 12/447237  
DATED : June 25, 2013  
INVENTOR(S) : Nicolas Merle et al.

Page 1 of 1

It is certified that error appears in the above-identified patent and that said Letters Patent is hereby corrected as shown below:

Title Page

Item (73), insert --Centre National de la Recherche Scientifique, Paris, France-- as assignee.

Item (57), in Abstract, replace "150° C. ;" with --150° C;--.

In the Claims

In col. 13, line 44, claim 1, replace "or and R'$_4$" with --or R'$_3$ and R'$_4$--.

Signed and Sealed this  
Twenty-second Day of October, 2013

Teresa Stanek Rea  
*Deputy Director of the United States Patent and Trademark Office*